(12) United States Patent
Qin et al.

(10) Patent No.: US 11,987,549 B2
(45) Date of Patent: May 21, 2024

(54) PREPARATION METHOD OF RHODIUM OCTANOATE DIMER

(71) Applicant: SHANGHAI OURCHEM BIO-TECHNOLOGY CO., LTD., Shanghai (CN)

(72) Inventors: Jianguo Qin, Shanghai (CN); Cong Wang, Shanghai (CN); Xin Sun, Shanghai (CN); Fang Ling, Shanghai (CN)

(73) Assignee: SHANGHAI OURCHEM BIO-TECHNOLOGY CO., LTD., Shanghai (CN)

( * ) Notice: Subject to any disclaimer, the term of this patent is extended or adjusted under 35 U.S.C. 154(b) by 492 days.

(21) Appl. No.: 17/298,956

(22) PCT Filed: Dec. 11, 2020

(86) PCT No.: PCT/CN2020/135742
§ 371 (c)(1),
(2) Date: Jun. 2, 2021

(87) PCT Pub. No.: WO2021/258663
PCT Pub. Date: Dec. 30, 2021

(65) Prior Publication Data
US 2022/0315518 A1  Oct. 6, 2022

(30) Foreign Application Priority Data
Jun. 24, 2020  (CN) .......................... 202010591490.2

(51) Int. Cl.
*C07C 51/41*  (2006.01)
(52) U.S. Cl.
CPC .................................. *C07C 51/418* (2013.01)
(58) Field of Classification Search
CPC .. C07C 51/418; C07C 53/126; C07F 15/0073
See application file for complete search history.

(56) References Cited

U.S. PATENT DOCUMENTS

2001/0043895 A1  11/2001  Schiodt

FOREIGN PATENT DOCUMENTS

| CN | 101353301 A | | 1/2009 |
|---|---|---|---|
| CN | 102786406 A | | 11/2012 |
| CN | 105669429 A | | 6/2016 |
| CN | 106905138 A | * | 6/2017 |
| CN | 106905138 A | | 6/2017 |
| CN | 109111357 A | * | 1/2019 |
| CN | 109111357 A | | 1/2019 |
| CN | 111718253 A | | 9/2020 |
| RU | 2182576 C2 | | 5/2002 |

OTHER PUBLICATIONS

Q. Ye, et al. 35 Transition Metal Chemistry 585-590 (2010) (Year: 2010).*
N. Anderson, Practical process research and development. Elsevier, (2000) (Year: 2000).*
MIT OpenCourseWare, 5.301 Chemistry Laboratory Techniques, 2012 (Year: 2012).*
Anne-Marie Giroud-Godquin, et al., Discotic Mesophases of Dirhodium Tetracarboxylates, J. Phys. Chem., 1986, pp. 5502-5503, 90.

* cited by examiner

*Primary Examiner* — Alexander R Pagano
*Assistant Examiner* — Frank S. Hou
(74) *Attorney, Agent, or Firm* — Bayramoglu Law Offices LLC

(57) ABSTRACT

A preparation method of a rhodium octanoate dimer includes the following steps: (1) mixing $RhCl_3$ with an alkali metal octanoate uniformly to get a first solution; (2) adding a reductant into the first solution obtained from step (1), and heating for reflux reaction to get a second solution; (3) adding the second solution obtained from step (2) into deionized water while hot, continuing to stir, and performing a suction filtration to get a crude product; and (4) performing a primary washing, a secondary washing, a filtration, and a drying on the crude product obtained from step (3) to get a rhodium octanoate dimer as a green solid.

16 Claims, No Drawings

PREPARATION METHOD OF RHODIUM OCTANOATE DIMER

CROSS REFERENCE TO THE RELATED APPLICATIONS

This application is the national phase entry of International Application No. PCT/CN2020/135742, filed on Dec. 11, 2020, which is based upon and claims priority to Chinese Patent Application No. 202010591490.2, filed on Jun. 24, 2020, the entire contents of which are incorporated herein by reference.

TECHNICAL FIELD

The present invention belongs to the technical field of the preparation of homogeneous catalysts, and particularly relates to a preparation method of a rhodium octanoate dimer.

BACKGROUND

Transition-metal catalysts (e.g., rhodium, palladium, ruthenium, etc.) achieve the transformation of straight chain compounds to cyclic compounds. The structures of rhodium (II) octanoate and rhodium (II) acetate are similar, a lantern structure with a double-stranded nucleic acid bridge. Rhodium octanoate dimer, as a homogeneous catalyst, has a significant catalytic activity on the C—H insertion reaction. Rhodium octanoate dimer is an important catalyst used in the field of medicine and chemical industry, and exhibits outstanding catalytic effects when being applied in cyclopropanation, hydroformylation, and other reactions. β-lactams can be generated from diazonamide under the catalysis of Rh (II), and this has become an important way of synthesizing β-lactams. Rhodium n-octanoate is just a critical catalyst for synthesizing such products. Giround-Godgium et al. firstly reported the synthesis of rhodium (II) octanoate in 1986 [J Phys. Chem.; 1986, 90, 5502]. The existing synthesis methods mainly include ligand exchange, Soxhlet extraction and the like. In the ligand exchange method for synthesizing rhodium (II) octanoate, the yield is relatively low, which is only 72% because rhodium (II) octanoate is highly soluble in octanoic acid and the boiling point of octanoic acid is substantially high (237° C.), and they are difficult to separate. Compared with rhodium (II) acetate, the Soxhlet extraction method for synthesizing rhodium (II) octanoate has a higher yield of 97.5%, but the energy consumption in Soxhlet extraction is high due to the high boiling point of octanoic acid, and there is a risk of pyrolysis of some products under such a high temperature. In addition, the Soxhlet extraction method is complex to operate, and the raw material rhodium acetate dimer is expensive and not readily available. The cost of the synthesized rhodium octanoate dimer is substantial as a result. Currently, the production process of rhodium n-octanoate catalysts in China is complex and outdated, and the resulting products are of low purity and yield, which cannot meet the requirements for large-scale industrial production.

In view of above deficiencies, the present invention is proposed.

SUMMARY

In order to overcome the defects of low yield, complex operation and high cost of raw materials in the preparation method of rhodium octanoate dimer in the prior art, the present invention provides a preparation method of a rhodium octanoate dimer, which is a two-step process, in which $RhCl_3$ and an alkali metal octanoate are firstly subject to ligand substitution to get an intermediate product rhodium (III) octanoate, and the rhodium (III) octanoate is then reduced to rhodium (II) octanoate with a weak reductant. This new process is simple to operate, the raw materials are readily available, and the yield of the resulting target product is high.

The present invention is realized by the following technical solution:

The reaction equation is:

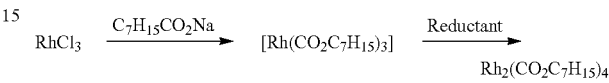

A preparation method of a rhodium octanoate dimer includes the following steps:
(1) mixing $RhCl_3$ with an alkali metal octanoate uniformly to get a first solution;
(2) adding a reductant into the first solution obtained from step (1), and heating for a reflux reaction to get a second solution;
(3) adding the second solution obtained from step (2) into deionized water while hot, continuing to stir, and performing a suction filtration to get a crude product; and
(4) performing a primary washing, a secondary washing, a filtration, and a drying on the crude product obtained from step (3) to get the rhodium octanoate dimer as a green solid.

Preferably, a molar ratio of the $RhCl_3$ to the alkali metal octanoate in step (1) is 1:(2.9-4.5).

Preferably, the alkali metal octanoate is one or more of sodium octanoate, potassium octanoate, lithium octanoate and cesium octanoate.

Preferably, a mass to volume ratio of the $RhCl_3$ to the reductant in the second solution in step (2) is 5.3:(100-300) g/mL; the reflux reaction is conducted at 70-80° C. for 4-12 h. As the reductant used is a weak reductant, the reflux reaction is performed for 4-12 h so as to ensure that the reduction reaction is complete, thus getting the rhodium (II) octanoate dimer.

Preferably, the reductant is one or more of ethanol, n-propanol, isopropanol, n-butanol, 2-butanol, isobutanol and n-pentanol.

Preferably, a volume of the deionized water in step (3) is 4 times that of the second solution, and the second solution is added into the deionized water slowly with stirring. As rhodium (II) octanoate is very insoluble in water, when the second solution obtained from the reflux reaction is added into the deionized water slowly, the green solid target product, rhodium (II) octanoate, is precipitated out.

Preferably, the primary washing in step (4) specifically includes: suspending the crude product in an aqueous solution of $NaHCO_3$ at 10 wt % with stirring for 1 h, and filtering to collect a solid. The by-products NaCl and sodium octanoate are water-soluble and can be removed after being dissolved in water.

Preferably, the secondary washing in step (4) specifically includes: resuspending the solid collected from the primary washing in diethyl ether with stirring for 1 h, and filtering to collect a solid. A small amount of by-product acetaldehyde is removed by washing with a diethyl ether beating method to finally obtain a final pure target product, rhodium (II) octanoate.

Preferably, the drying in step (4) is conducted in a vacuum drying oven at 50-80° C. for 10 h until a constant weight is reached.

Compared to the prior art, the present invention has the following advantages:
(1) In the present invention, by employing a two-step process, $RhCl_3$ and an alkali metal octanoate are firstly subject to ligand substitution to get an intermediate product rhodium (III) octanoate, and the rhodium (III) octanoate is then reduced to rhodium (II) octanoate with a weak reductant. This process is simple to operate, the raw materials are readily available, and the resulting target product may have a high purity (higher than 98%) and a high yield (a total yield of greater than 80%), which can meet the requirements for industrial production.
(2) The weak reductant used in the present invention, including ethanol, n-propanol, isopropanol, n-butanol, 2-butanol, isobutanol or n-pentanol and the like, ensures that all of the trivalent rhodium can be reduced to divalent rhodium, but at the same time the trivalent rhodium will not be over-converted into metal rhodium, thus improving the yield of the target product.
(3) The post-processing steps of the present invention are simple, and the raw materials are readily available and have no pollution. As rhodium (II) octanoate is very insoluble in water, when the second solution obtained from the reflux reaction is added into deionized water slowly, the green solid target product, rhodium (II) octanoate, is precipitated out. By a primary washing step, the crude product is suspended in an aqueous solution of $NaHCO_3$ at 10 wt % to remove the by-products NaCl and sodium octanoate (water-soluble). By a secondary washing step (diethyl ether beating method), acetaldehyde is removed to finally obtain the target product with a high purity.

DETAILED DESCRIPTION OF THE EMBODIMENTS

The technical solution of the present invention will be described clearly and completely in the following embodiments. Obviously, the described embodiments are only a part of embodiments in the present invention, not all the embodiments. The description of at least one of the exemplary embodiments below is only illustrative in fact, and in no way restricts the present invention and its application or use. All other embodiments attained by those with ordinary skills in the art on the basis of the embodiments in the present invention without any creative labors are covered within the protection scope of the present invention.

In addition, it should be noted that the utilization of "first", "second" and other words for defining the solutions obtained in different steps is only for ease of distinguishing the solutions produced in various reaction steps. Unless otherwise stated, the above words have no special meanings, and they should not be construed as the limitation on the protection scope of the present invention.

Embodiment 1

A preparation method of a rhodium octanoate dimer, including the following steps:

(1) 5.3 g (25.3 mmol) $RhCl_3$ and 12.3 g (74 mmol) sodium octanoate (an alkali metal octanoate) were added into a 500 mL single-neck flask and mixed uniformly to get a first solution.
(2) 200 mL ethanol (a reductant) was added into the first solution obtained from step (1), and heated to 80° C. for reflux reaction for 4 h, to get a second solution in dark-green.
(3) With stirring, the second solution obtained from step (2) was added into 800 mL deionized water slowly while hot, and then a large amount of dark-green solid was precipitated out immediately. After the addition, they were continually stirred for 1 h and subjected to a suction filtration to get a crude product as a green solid.
(4) The crude product obtained from step (3) was suspended in 400 mL aqueous solution of $NaHCO_3$ at 10 wt % with stirring for 1 h; the water-soluble by-products, NaCl and sodium octanoate, were removed by thoroughly washing (primary washing), and the solid was collected by filtration; the solid collected after the primary washing was resuspended in 200 mL diethyl ether with stirring for 1 h; the by-product acetaldehyde was removed by employing a diethyl ether beating process (secondary washing), and the solid was collected by filtration, dried in a vacuum drying oven at 50° C. for 10 hours until a constant weight is reached, to obtain 8.2 g of a target product rhodium octanoate dimer with a yield of 83.2%, and a purity greater than 98% detected by high performance liquid chromatography (HPLC).

Embodiment 2

A preparation method of a rhodium octanoate dimer, including the following steps:

(1) 4.4 g (21.2 mmol) $RhCl_3$ and 12.3 g (74 mmol) sodium octanoate (an alkali metal octanoate) were added into a 500 mL single-neck flask and mixed uniformly to get a first solution.
(2) 100 mL n-butanol (a reductant) was added into the first solution obtained from step (1), and heated to 70° C. for reflux reaction for 8 h, to get a second solution in dark-green.
(3) With stirring, the second solution obtained from step (2) was added into 800 mL deionized water slowly while hot, and then a large amount of dark-green solid was precipitated out immediately. After the addition, they were continually stirred for 1 h and subjected to a suction filtration to get a crude product as a green solid.
(4) The crude product obtained from step (3) was suspended in 400 mL aqueous solution of $NaHCO_3$ at 10 wt % with stirring for 1 h; the water-soluble by-products, NaCl and sodium octanoate, were removed by thoroughly washing (primary washing), and the solid was collected by filtration; then the solid collected after the primary washing was resuspended in 200 mL diethyl ether with stirring for 1 h; the by-product acetaldehyde was removed by employing a diethyl ether beating process (secondary washing), and the solid was collected by filtration, dried in a vacuum drying oven at 60° C. for 10 hours until a constant weight is reached, to obtain 7.0 g of a target product rhodium octanoate dimer with a yield of 85%, and a purity greater than 98% detected by HPLC.

Embodiment 3

A preparation method of a rhodium octanoate dimer, including the following steps:

(1) 5.3 g (25.3 mmol) $RhCl_3$ and 18.9 g (113.7 mmol) sodium octanoate (an alkali metal octanoate) were added into a 500 mL single-neck flask and mixed uniformly to get a first solution;

(2) 300 mL isopropanol (a reductant) was added into the first solution obtained from step (1), and heated to 80° C. for reflux reaction for 12 h, to get a second solution in dark-green;

(3) With stirring, the second solution obtained from step (2) was added into 800 mL deionized water slowly while hot, and then a large amount of dark-green solid was precipitated out immediately. After the addition, they were continually stirred for 1 h and subjected to a suction filtration to get a crude product as a green solid;

(4) The crude product obtained from step (3) was suspended in 400 mL aqueous solution of $NaHCO_3$ at 10 wt % with stirring for 1 h; the water-soluble by-products, NaCl and sodium octanoate, were removed by thoroughly washing (primary washing), and the solid was collected by filtration; then the solid collected after the primary washing was resuspended in 200 mL diethyl ether with stirring for 1 h; the by-product acetaldehyde was removed by employing a diethyl ether beating process (secondary washing), and the solid was collected by filtration, dried in a vacuum drying oven at 60° C. for 10 hours until a constant weight is reached, to obtain 8.7 g of a target product rhodium octanoate dimer with a yield of 88%, and a purity greater than 98% detected by HPLC.

Comparative Embodiment 1

The reductant ethanol used in step (2) of embodiment 1 was replaced with hydrazine hydrate, with other operations all the same as in embodiment 1. The results showed that a black precipitate appeared immediately after adding hydrazine hydrate, indicating that hydrazine hydrate reduced trivalent rhodium metal ions to a non-valent metal rhodium within a very short time. This may be because that hydrazine hydrate is too reductive to produce the target product rhodium (II) octanoate dimer.

Comparative Embodiment 2

The reductant ethanol used in step (2) of embodiment 1 was replaced with an organic reductant triphenylphosphine with weak reducing capacity, with other operations all the same as in embodiment 1. The results showed that after the reflux reaction, a dark-green solution was obtained, and a small amount of black precipitates appeared at the bottom of the flask, indicating that most of the reaction products were the target product rhodium (II) octanoate dimer, but there was still a phenomenon of partial over-reduction in which trivalent rhodium metal ions were directly reduced to metal rhodium.

The present invention employs a two-step process in which $RhCl_3$ and alkali metal octanoate are subjected to ligand substitution to get an intermediate product rhodium (III) octanoate, and the rhodium (III) octanoate is then reduced to rhodium (II) octanoate with a weak reductant. This process is simple to operate, the raw materials are readily available, and the resulting target product has a high purity (higher than 98%) and a high yield (a total yield of greater than 80%), which can meet the requirements for industrial production.

The weak reductant used in the present invention, including ethanol, n-propanol, isopropanol, n-butanol, 2-butanol, isobutanol or n-pentanol and the like, ensures that all of the trivalent rhodium can be reduced to divalent rhodium, but at the same time the trivalent rhodium will not be over-converted into metal rhodium, thus improving the yield of the target product.

(3) The post-processing steps of the present invention are simple, and the raw materials are readily available and have no pollution.

The objective, technical solution and advantages of the present invention have been further illustrated in detail in the above specific embodiments. It should be noted that the foregoing description only shows specific embodiments of the present invention, rather than the limitation of the present invention. Any modifications, equivalent replacements, and improvements made within the spirit and principle of the present invention shall all fall within the protection scope of the present invention.

What is claimed is:

1. A preparation method of a rhodium octanoate dimer, comprising the following steps:
   (1) mixing $RhCl_3$ with an alkali metal octanoate uniformly to get a first solution;
   (2) adding a reductant into the first solution obtained from step (1) to obtain a first mixture, and heating the first mixture for a reflux reaction to get a second solution wherein the reductant is at least one selected from the group consisting of n-butanol, 2-butanol, isobutanol and n-pentanol;
   (3) adding the second solution obtained from step (2) into deionized water while hot to obtain a second mixture, continuing to stir the second mixture, and performing a suction filtration on the second mixture to get a crude product, and
   (4) performing a primary washing, a secondary washing, a filtration, and a drying on the crude product obtained from step (3) to get the rhodium octanoate dimer as a green solid.

2. The preparation method of the rhodium octanoate dimer according to claim 1, wherein a molar ratio of the $RhCl_3$ to the alkali metal octanoate in step (1) is 1:(2.9-4.5).

3. The preparation method of the rhodium octanoate dimer according to claim 1, wherein the alkali metal octanoate is at least one selected from the group consisting of sodium octanoate, potassium octanoate, lithium octanoate and cesium octanoate.

4. The preparation method of the rhodium octanoate dimer according to claim 1, wherein a mass to volume ratio of the $RhCl_3$ to the reductant in the second solution in step (2) is 5.3:(100-300) g/mL; and the reflux reaction is conducted at 70-80° C. for 4-12 h.

5. The preparation method of the rhodium octanoate dimer according to claim 1, wherein a volume of the deionized water in step (3) is 4 times a volume of the second solution, and the second solution is added into the deionized water slowly with a stirring.

6. The preparation method of the rhodium octanoate dimer according to claim 1, wherein the primary washing in step (4) specifically comprises: suspending the crude product in an aqueous solution of $NaHCO_3$ at 10 wt % with a stirring for 1 h to obtain a first product, and filtering the first product to collect a first solid.

7. The preparation method of the rhodium octanoate dimer according to claim 1, wherein the secondary washing in step (4) specifically comprises: resuspending a first solid collected from the primary washing in diethyl ether with a stirring for 1 h to obtain a second product, and filtering the second product to collect a second solid.

8. The preparation method of the rhodium octanoate dimer according to claim 1, wherein the drying in step (4) is conducted in a vacuum drying oven at 50-80° C. for 10 h until a constant weight of the rhodium octanoate dimer is reached.

9. The preparation method of the rhodium octanoate dimer according to claim 2, wherein the alkali metal octanoate is at least one selected from the group consisting of sodium octanoate, potassium octanoate, lithium octanoate and cesium octanoate.

10. The preparation method of the rhodium octanoate dimer according to claim 1, wherein the alkali metal octanoate is potassium octanoate.

11. The preparation method of the rhodium octanoate dimer according to claim 1, wherein the alkali metal octanoate is lithium octanoate.

12. The preparation method of the rhodium octanoate dimer according to claim 1, wherein the alkali metal octanoate is cesium octanoate.

13. The preparation method of the rhodium octanoate dimer according to claim 1, wherein the reductant is n-butanol.

14. The preparation method of the rhodium octanoate dimer according to claim 1, wherein the reductant is 2-butanol.

15. The preparation method of the rhodium octanoate dimer according to claim 1, wherein the reductant is isobutanol.

16. The preparation method of the rhodium octanoate dimer according to claim 1, wherein the reductant is n-pentanol.

* * * * *